United States Patent
Pugia

(10) Patent No.: US 10,444,240 B2
(45) Date of Patent: Oct. 15, 2019

(54) RARE CELL CONCENTRATION

(71) Applicant: SIEMENS HEALTHCARE DIAGNOSTICS INC., Tarrytown, NY (US)

(72) Inventor: Michael Pugia, Granger, IN (US)

(73) Assignee: SIEMENS HEALTHCARE DIAGNOSTICS, INC., Tarrytown, NY (US)

( * ) Notice: Subject to any disclaimer, the term of this patent is extended or adjusted under 35 U.S.C. 154(b) by 76 days.

(21) Appl. No.: 14/780,937

(22) PCT Filed: Mar. 26, 2014

(86) PCT No.: PCT/US2014/031895
§ 371 (c)(1),
(2) Date: Sep. 28, 2015

(87) PCT Pub. No.: WO2014/160796
PCT Pub. Date: Oct. 2, 2014

(65) Prior Publication Data
US 2016/0054326 A1    Feb. 25, 2016

Related U.S. Application Data

(60) Provisional application No. 61/806,581, filed on Mar. 29, 2013.

(51) Int. Cl.
| | | |
|---|---|---|
| *G01N 33/574* | (2006.01) | |
| *G01N 33/50* | (2006.01) | |
| *G01N 33/569* | (2006.01) | |
| *G01N 33/86* | (2006.01) | |
| *G01N 33/53* | (2006.01) | |
| *C12Q 1/56* | (2006.01) | |

(52) U.S. Cl.
CPC ......... *G01N 33/57488* (2013.01); *C12Q 1/56* (2013.01); *G01N 33/5091* (2013.01); *G01N 33/5306* (2013.01); *G01N 33/56966* (2013.01); *G01N 33/574* (2013.01); *G01N 33/86* (2013.01)

(58) Field of Classification Search
None
See application file for complete search history.

(56) References Cited

U.S. PATENT DOCUMENTS

| 6,365,362 B1 | 4/2002 | Terstappen et al. |
| 7,166,443 B2 | 1/2007 | Walker et al. |
| 2002/0164825 A1* | 11/2002 | Chen ................ G01N 33/56966 436/526 |
| 2005/0014128 A1* | 1/2005 | Ewert ...................... C12Q 1/04 435/2 |
| 2010/0247492 A1 | 9/2010 | Kuhn |
| 2011/0070642 A1* | 3/2011 | Cayre ................... C12M 47/04 435/325 |

FOREIGN PATENT DOCUMENTS

| WO | WO-2012035508 A2 * | 3/2012 | ....... G01N 33/56938 |

OTHER PUBLICATIONS

Dvorak, H.F. et al. 1983. Fibrin as a component of the tumor stroma: origins and biological significance. Cancer Metastasis Reviews 2: 41-73. specif. pp. 41, 54.*
Konstantopoulos, K. et al. 2009. Cancer cells in transit: the vascular interactions of tumor cells. Annual Review of Biomedical Engineering 11: 177-202. specif. pp. 177, 194.*
Isabelle Desitter et al; "A New Device for Rapid Isolation by Size and Characterization of Rare Circulating Tumor Cells"; Anticancer Research; Feb. 1, 2011, vol. 31; No. 2; pp. 427-442.
European Search Report for EP Application No. 14776499.7, dated Oct. 26, 2016.
European Search Report from International Application No. PCT/US14/31895, dated Aug. 8, 2014.

* cited by examiner

*Primary Examiner* — Renee Claytor
*Assistant Examiner* — Sharon M. Papciak
(74) *Attorney, Agent, or Firm* — Kevin Stein

(57) ABSTRACT

A ratio of rare cells to non-rare cells in a blood sample suspected of containing rare cells and non-rare cells is enhanced. A treated blood sample is prepared by providing in combination the blood sample, a platelet deactivation agent, a fibrin-formation-arresting agent and fibrin in an amount sufficient to cause a predetermined level of agglutination of the rare cells. The treated blood sample is then contacted with a porous matrix such that agglutinated rare cells are preferentially retained on the porous matrix. The rare cells may then be identified.

17 Claims, 2 Drawing Sheets

RARE CELL CONCENTRATION

CROSS-REFERENCE TO RELATED APPLICATIONS

This application claims priority to U.S. Provisional Application Ser. No. 61/806,581 filed Mar. 29, 2013, which is incorporated herein by reference in its entirety.

BACKGROUND

The invention relates to methods and kits for increasing a ratio of rare cells to non-rare cells in a blood sample and for identifying the rare cells. More particularly, the invention relates to methods and kits for increasing a ratio of cancer cells to white blood cells in a blood sample and for identifying the cancer cells.

Cell filtration for the separation of cancer cells using a porous matrix is used to sort cells by size and, in most instances, such filtration methods allow for the extraction of cells following separation. Both microfluidic post and microfluidic membrane methods are used in these filtration approaches. However, the existing filtration methods are limited by certain factors, which include, for example, the range of diameters that in vitro cells have rather than a single diameter. This range of diameters is demonstrated, for example, in the case of cancer cell populations and white blood cell populations, which have overlapping diameters. During filtration small cancer cells are lost and larger white blood cells contaminate the separated material. Furthermore, cancer cell populations and white blood cell populations are very heterogeneous and comprise a variety of cell diameter types within these individual populations. For example, the range of diameters for white blood cells is much wider when considering samples including populations of neutrophils, eosinophils, basophils, macrophages, lymphocytes and macrophages. Cancer cells in blood can also range in size.

Another limitation on the selectivity of a cell filtration method is that ideal pore size is impacted by the deformability of various cells. This deformability further reduces selectivity for size exclusion to isolate different cells. A small diameter cell with low deformability requires the use of a matrix having even a smaller pore size than otherwise might be used. Using smaller pore sizes increases the number of desired cells captured (e.g., cancer cells) but results in a less pure separation. Furthermore, when the pores are made smaller, they are prone to clogging. Pressure increases as pore size decreases. Clogging and higher pressure can be temporarily reduced by an oscillatory flow force (on/off). Preventing a pressure from building across the separation microstructure is important as higher pressures reduce the impact of cell size on separation.

In addition, blood cells are typically fixed before separation by filtration to improve separation of the cells. Recovery of target cells is reduced when fixation is not used since some target cells have higher deformability than other target cells. Fixation causes all cells to have similar deformability (viscoelastic properties). However, there are a number of disadvantages to fixing cells such as, for example, the requirement of greater pressure for passage of the fixed cells through a porous matrix. As pressure increases, ideal pore size decreases. Smaller pores lead to greater capture of undesired cells. Another disadvantage is that fixed cells are not viable and cannot be grown or used to measure cells responses to stimulus.

There is, therefore, a need to develop a filtration separation method that does not require fixation. The method should improve cell recovery and be independent of differences in cell diameter and differences in viscoelastic properties.

SUMMARY

Some examples in accordance with the principles described herein are directed to methods of increasing a ratio of rare cells to non-rare cells in a blood sample suspected of containing rare cells and non-rare cells. A treated blood sample is prepared by providing in combination the blood sample, a platelet deactivation agent, a fibrin-formation-arresting agent and fibrin in an amount sufficient to cause a predetermined level of agglutination of the rare cells. The treated blood sample is then contacted with a porous matrix such that agglutinated rare cells are preferentially retained on the porous matrix.

Some examples in accordance with the principles described herein are directed to methods of increasing a ratio of cancer cells to non-cancer cells in a blood sample suspected of containing cancer cells and non-cancer cells. In the method a treated blood sample is prepared by combining the blood sample, a platelet deactivation agent, a fibrin-formation-arresting agent, and fibrin in an amount sufficient to cause agglutination of the rare cells in an amount of about 2.5% to about 100% based on an amount of surface area of the rare cells covered with large fibrin. The treated blood sample is diluted with a dilution medium, and disposed on a side of a porous matrix. Pressure is applied to the disposed treated blood sample and agglutinated cancer cells are preferentially retained on the porous matrix.

Some examples in accordance with the principles described herein are directed to methods of identifying at least one rare cell type in a blood sample suspected of containing the rare cell type. A combination is provided comprising the blood sample, a platelet deactivation agent, a fibrin-formation-arresting agent, and fibrin in an amount of about 0.2 mg/L to about 10 mg/L based on the volume of the blood sample to cause agglutination of the rare cells and to prepare a treated blood sample. Following dilution of the treated blood sample with a dilution medium, the diluted treated blood sample is contacted with a porous matrix such that agglutinated rare cells are preferentially retained on the porous matrix. Then, the rare cells are contacted with an identification agent to identify the rare cells.

BRIEF DESCRIPTION OF THE DRAWINGS

The drawings provided herein are not to scale and are provided for the purpose of facilitating the understanding of certain examples in accordance with the principles described herein and are provided by way of illustration and not limitation on the scope of the appended claims.

DETAILED DESCRIPTION OF SPECIFIC EMBODIMENTS

General Discussion

Figure 1:
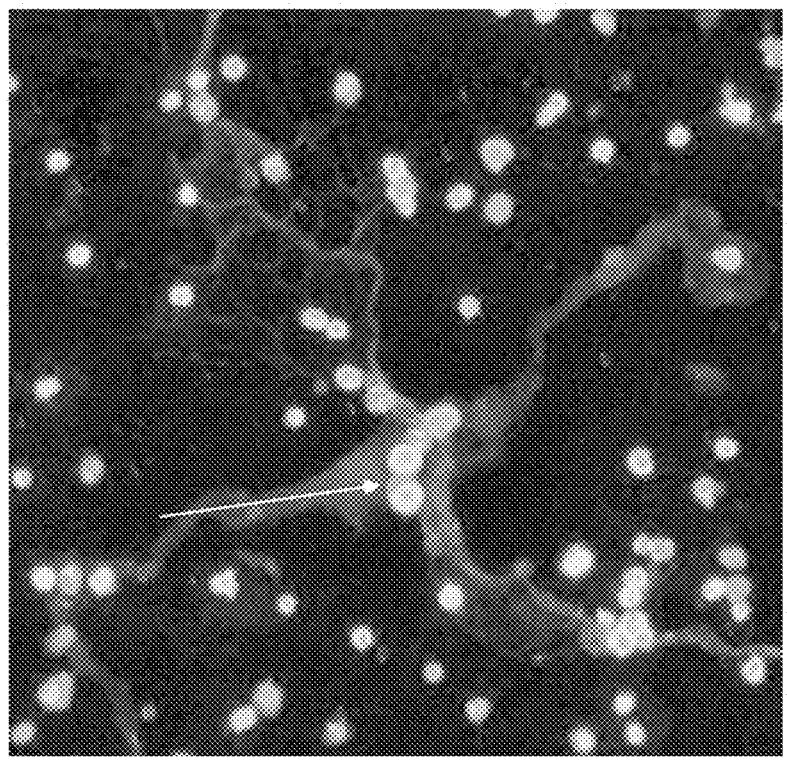
FIG. 1 represents a visualization of cells and fibrin using direct immunofluorescence based on experiments described in the Examples section below, which were conducted in accordance with the principles described herein. The visualization corresponds to the results summarized in Table 1 for Sample Type 3.

Examples in accordance with the principles described herein permit separation of different cell types such as, for example, cancer cells from white blood cells. A blood sample suspected of containing the different cell types is treated to minimize platelet formation and to arrest the formation of fibrin resulting from the coagulation of the blood resulting from natural blood clotting factors present in the blood sample. Fibrin is added to the blood sample to obtain a predetermined level of agglutination of one or more of the different cell types over other cell types in the blood sample. The predetermined level of agglutination of some of the different cell types allows a diluted blood sample treated as described above to be filtered through a porous matrix with relatively small pore sizes. Agglutinated cells are retained on the porous matrix after filtration and non-agglutinated cells, which are primarily undesirable cells, pass through the porous matrix.

The separation achieved in accordance with the principles described herein is independent of the viscoelastic properties of the cells and of the diameter of the cells. Furthermore, the methods in accordance with the principles described herein work for fixed and non-fixed live cells. In addition, the methods in accordance with the principles described herein avoid variable amounts of fibrin formed among different subjects for one or more reasons relating to short-comings that may arise in the natural coagulation cascade of the different subjects.

Rare cells are those cells that are present in a sample in relatively small quantities when compared to the amount of non-rare cells in a sample. In some examples, the rare cells are present in an amount of about $10^{-8}$% to about $10^{-2}$% by weight of a total cell population in a sample suspected of containing the rare cells. The rare cells may be, but are not limited to, malignant cells such as malignant neoplasms or cancer cells; circulating endothelial cells; circulating epithelial cells; fetal cells; immune cells (B cells, T cells, macrophages, NK cells, monocytes); stem cells; nucleated red blood cells (normoblasts or erythroblasts); and immature granulocytes; for example.

Non-rare cells are those cells that are present in relatively large amounts when compared to the amount of rare cells in a sample. In some examples, the non-rare cells are at least about 10 times, or at least about $10^2$ times, or at least about $10^3$ times, or at least about $10^4$ times, or at least about $10^5$ times, or at least about $10^6$ times, or at least about $10^7$ times, or at least about $10^8$ times greater than the amount of the rare cells in the total cell population in a sample suspected of containing non-rare cells and rare cells. The non-rare cells may be, but are not limited to, white blood cells, platelets, and red blood cells, for example.

The sample to be tested is a blood sample from a mammal such as, but not limited to, a human subject, for example. The blood sample is one that contains cells such as, for example, non-rare cells and rare cells. In some examples the blood sample is whole blood or plasma.

Samples are collected from the body of a subject into a suitable container such as, but not limited to, a bag, a bottle, a needle or a VACUTAINER® container, for example. The container may contain a collection medium into which the sample is delivered. The collection medium is usually a dry medium and may comprise an amount of platelet deactivation agent effective to achieve deactivation of platelets in the blood sample when mixed with the blood sample. The collection medium may also comprise a fibrin-formation-arresting agent in an amount sufficient to arrest the formation of fibrin from naturally occurring proteins in the blood sample.

Platelet deactivation agents include, but are not limited to, chelating agents such as, for example, chelating agents that comprise a triacetic acid moiety or a salt thereof, a tetraacetic acid moiety or a salt thereof, a pentaacetic acid moiety or a salt thereof, or a hexaacetic acid moiety or a salt thereof. In some examples, the chelating agent is ethylene diamine tetraacetic acid (EDTA) and its salts or ethylene glycol tetraacetate (EGTA) and its salts. The effective amount of platelet deactivation agent is dependent on one or more of the nature of the platelet deactivation agent, the nature of the blood sample, level of platelet activation and ionic strength, for example. In some examples, for EDTA as the anti-platelet agent, the amount of dry EDTA in the container is that which will produce a concentration of about 1.0 to about 2.0 mg/mL of blood, or about 1.5 mg/mL of the blood. The amount of the platelet deactivation agent is that which is sufficient to achieve at least about 90%, or at least about 95%, or at least about 99% of platelet deactivation.

As mentioned above, the blood sample is also combined with a fibrin-formation-arresting agent, which may be present in a blood collection container or added subsequent to the collection of the blood sample. The fibrin-formation-arresting agent is a substance that, when combined with the blood sample, stops the formation of fibrin on the surface of the rare cells, which forms as a result of the presence in the blood sample of naturally occurring clotting proteins such as, for example, fibrinogen. Such fibrin-formation-arresting agents include, for example, platelet deactivation agents, anti-coagulants and fixing agents.

Platelet deactivation agents include those mentioned above. In some examples, the platelet deactivation agent is, but is not limited to, chelators such as, e.g., EDTA; citrate; cyclooxygenase inhibitors; adenosine diphosphate (ADP) receptor inhibitor; glycoprotein IIB/IIIA inhibitors; phosphodiesterase inhibitors; thromboxane inhibitors; and adenosine reuptake inhibitors, for example.

Anti-coagulants include, but are not limited to, Factor VII inhibitors, Factor X inhibitors, direct thrombin inhibitors, coumarins, heparin, and antithrombin proteins, for example.

Fixing agents include, but are not limited to, substances that act to cross-link proteins and/or to disable proteolytic enzymes and prevent natural generation of fibrin. In some examples, the fixing agent is an aldehyde reagent (such as, e.g., formaldehyde, glutaraldehyde, and paraformaldehyde) and ureas (such as, e.g., diazolidinyl urea or imidazolidinyl urea).

An amount of fibrin-formation-arresting agent employed is dependent on a number of factors such as, for example, the nature of the fibrin-formation-arresting agent, the number of cells in the sample, the nature of the blood sample, level of platelet deactivation, level of activation of coagulation, and ionic strength. The normal range for fibrin in blood is 0.22 to 0.50 µg/mL (mg/L), which translates into 110 to 250 ng/mL D Dimer, a protein fragment or degradation product of fibrin resulting from degradation of fibrin by fibrinolysis. Abnormal values for fibrin in blood are 0.5 to 5.0 mg/L, which translates into values 250 to 2500 ng/mL for D DIMER. Fibrin precursor, fibrinogen, is normally present at a concentration of 1.5-4.0 g/L. In some examples in accordance with the principles described herein, the amount of fibrin-formation-arresting agent is about 0.01% to about 0.5%, or about 0.01% to about 0.4%, or about 0.01% to about 0.3%, or about 0.01% to about 0.2%, or about 0.01% to about 0.1%, or about 0.1% to about 0.5%, or about 0.1% to about 0.4%, or about 0.1% to about 0.3%, or about 0.1% to about 0.2%, for example, by weight of the blood sample. The amount of the fibrin-formation-arresting agent is that which is sufficient to reduce the formation of fibrin to no more than about 0.5 mg/L, or no more than about 0.4% mg/L, or no more than about 0.3% mg/L, or no more than about 0.2% mg/L, or no more than about 0.1% mg/L, for example, of blood sample. In some examples, the fibrin-formation-arresting agent is employed in the collection medium as a dry reagent.

The collection medium may also contain one or more additional agents such as, but not limited to, $CrCl_3$ or $MnCl_2$, dextrose, glucose, citrate, adenosine triphosphate, inosine, dihydroxyacetone, 2,3-diphosphoglycerol, chloramphenicol, neomycin sulphate, magnesium chloride, iodoacetamide, sodium ascorbate, acetic acid, dimethylsulfoxide, zinc sulfate, 2-bromo-2-nitropropane-1,3-diol, urea and urea derivatives, acetamide, formamide, hydantoin, alcohols, acetic acid, formic acid, dehydrated oxidant (osmium), HEPES-glutamic acid buffer-mediated organic solvent protection effect (HOPE) (Polysciences, Inc.), diimidoester fixation agents using dimethyl suberimidate (DMS), growth factors transferrin inhibitors, and inhibitors for phosphorylation and other enzymes, for example. These additional agents, if present, are present in amounts that achieve their respective intended purposes. In some examples the collection medium is a standard blood collection or anti-coagulant medium.

The blood sample is also combined with fibrin, either simultaneously or sequentially, with the other agents in the collection medium as set forth above or after the blood sample is collected in the collection medium. Fibrin (Factor Ia) is a fibrous, non-globular protein formed from fibrinogen by the protease thrombin and then polymerized to form a clot with platelets over a wound site. Fibrinogen is synthesized in the liver and is circulated in plasma at about 200 mg/dL to about 450 mg/dL. Fibrin is a dimeric glycoprotein composed of three pairs of peptide chains. The two subunits are composed of a D domain that comprises a globular region and an E domain that comprises a disulfide bond that links the two subunits. The molecular mass of the soluble dimer is: 340 kilodaltons (kDa) ($\alpha$ chain: 63.5 kDa, $\beta$ chain: 56 kDa, $\gamma$ chain: 47 kDa). Fibrin is glycosylated with complex type biantennary asparagine linked glycans that vary in the degree of core fucosylation and types of sialic acid and galactose linkage. Fibrin is available commercially from, for example, Sigma-Aldrich Corporation, St. Louis Mo.

Added fibrin is employed in an amount sufficient to cause a predetermined level of agglutination of the rare cells. The amount of fibrin and the predetermined level of agglutination of the rare cells are dependent on a number of factors such as, for example, the number of cells in the blood sample, the nature of the blood sample, the level of platelet activation, and the level of activation of coagulation or clotting. The phrase "level of agglutination" refers to the percentage (%) of cells with large fibrin on the surface. In some examples in accordance with the principles described herein, the predetermined level of agglutination of the rare cells is about 2% to about 100%, or about 2% to about 80%, or about 2% to about 60%, or about 2% to about 50%, or about 2% to about 40%, or about 2% to about 30%, or about 2% to about 20%, or about 2% to about 10%, or about 2% to about 8%, or about 2% to about 5%, or about 5% to about 10%, or about 5% to about 8%, for example, based on the area of the outer surface of the rare cells. In some examples the percentage of cells having large fibrin on the surface is no more than about 20%, or no more than about 15%, or no more than about 10% to control the level of cell-cell agglutination. In some examples the percentage of cells having large fibrin on the surface should be in a range of about 2% to about 10%. The phrase "large fibrin" refers to the extent of network formation by fibrin filaments having a size that is larger than the size of a cell itself.

In some examples in accordance with the principles described herein, the amount of fibrin added is about 0.2 mg/L to about 10 mg/L, or about 0.2 mg/L to about 7.5 mg/L, or about 0.2 mg/L to about 5.0 mg/L, or 0.2 mg/L to about 2.5 mg/L, or about 0.2 mg/L to about 1.0 mg/L, or about 0.5 mg/L to about 10 mg/L, or about 0.5 mg/L to about 7.5 mg/L, or about 0.5 mg/L to about 5.0 mg/L, or 0.5 mg/L to about 2.5 mg/L, or about 0.5 mg/L to about 1.0 mg/L, or about 1.0 mg/L to about 10 mg/L, or about 1.0 mg/L to about 7.5 mg/L, or about 1.0 mg/L to about 5.0 mg/L, or 1.0 mg/L to about 2.5 mg/L, or about 2 mg/L to about 10 mg/L, or about 2 mg/L to about 7.5 mg/L, or about 2 mg/L to about 5.0 mg/L, based on the volume of the blood sample. The fibrin is employed as a dry reagent, e.g., in the collection medium, or is present in, for example, an aqueous medium.

In examples in accordance with the principles described herein, the cell-cell agglutination should be minimized. The phrase "cell-cell agglutination" refers to cells that are in contact with one another.

The blood sample is maintained under conditions for fibrin formation on a surface of the rare cells to cause a predetermined level of agglutination of the rare cells. These conditions include holding the blood sample at a temperature of about 4° C. to about 35° C., or about 4° C. to about 30° C., or about 4° C. to about 25° C., or about 4° C. to about 20° C., or about 4° C. to about 15° C., or about 4° C. to about 10° C., or about 10° C. to about 35° C., or about 10° C. to about 30° C., or about 10° C. to about 25° C., or about 10° C. to about 20° C., or about 10° C. to about 15° C., for example. The time period is about 0 seconds to about 10 days, or about 10 seconds to about 10 days, or about 1 minute to about 10 days, or about 10 minutes to about 10 days, or about 30 minutes to about 10 days, or about 1 hour to about 10 days, or about 5 hours to about 10 days, or about 10 hours to about 10 days, or about 1 day to about 10 days, or about 0 seconds to about 5 days, or about 10 seconds to about 5 days, or about 1 minute to about 5 days, or about 10 minutes to about 5 days, or about 30 minutes to about 5 days, or about 1 hour to about 5 days, or about 5 hours to about 5 days, or about 10 hours to about 5 days, or about 1 day to about 5 days, or about 0 seconds to about 1 day, or about 10 seconds to about 1 day, or about 1 minute to about 1 day, or about 10 minutes to about 1 day, or about 30 minutes to about 1 day, or about 1 hour to about 1 day, or about 5 hours to about 1 day, or about 10 hours to about 1 day, for example.

The level of agglutination of the rare cells can be controlled by the amount of fibrin added to the blood sample. In some instances it may be necessary to stop the fibrin-induced agglutination of the rare cells so that the predetermined level of agglutination of the rare cells is attained. In some examples, the action of fibrin may be stopped by employing a specific binding partner for fibrin, which may be, for example, an antibody specific for fibrin. An antibody for fibrin may be directed at an epitope of the fibrin molecule or at an epitope of a fragment of fibrin resulting from degradation of fibrin such as, for example, the D Dimer, which, as mentioned above, is a protein fragment or degradation product of fibrin resulting from degradation of fibrin by fibrinolysis. Antibodies specific for fibrin for use in monitoring fibrin formation can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab)$_2$, and Fab', for example. In addition, aggregates, polymers, and conjugates of immunoglobulins or their fragments can be used where appropriate so long as binding affinity for a particular molecule is maintained.

In some examples, the antibody may comprise a label, the nature of which is dependent on the particular assay format chosen for monitoring fibrin formation. The label, which is discussed in more detail below in the general description of assays, is any molecule that produces or can be induced to produce a signal, and may be, for example, a fluorescer, a radiolabel, an enzyme, a chemiluminescer or a photosensitizer. Thus, the signal is detected and/or measured by detecting enzyme activity, luminescence, light absorbance or radioactivity, depending on the nature of the label. The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes. In some examples, the label is part of a signal producing system, which may include components other than the label for generating a signal in conjunction with the label. In some examples the labeled antibody stains the fibrin.

After addition of the antibody for fibrin, the treated blood sample is maintained under conditions for binding of the antibody to the fibrin. These conditions include holding the mixture of fibrin antibody and blood sample at a temperature of about 20° C. to about 38° C., or about 20° C. to about 35° C., or about 20° C. to about 30° C., or about 20° C. to about 25° C., or about 25° C. to about 35° C., or about 25° C. to about 30° C., for a period of about 5 minutes to about 1 hour, or about 5 minutes to about 45 minutes, or about 5 minutes to about 30 minutes, or about 5 minutes to about 20 minutes, or about 5 minutes to about 10 minutes, or about 10 minutes to about 1 hour, or about 10 minutes to about 45 minutes, or about 10 minutes to about 30 minutes, or about 10 minutes to about 20 minutes, for example.

Following the treatment of the blood sample with the fibrin and other agents as described above, the blood sample is contacted with a porous matrix such that agglutinated rare cells are preferentially retained on the porous matrix and non-rare cells pass through the porous matrix. In some examples in accordance with the principles described herein, the treated blood sample is diluted with a dilution medium prior to contact with the porous matrix. In some examples, the dilution medium is an aqueous medium, which may be buffered. The pH for an aqueous buffered medium is usually a moderate pH. In some examples the pH of the dilution medium is about 5 to about 8, or about 6 to about 8, or about 7 to about 8, or about 5 to about 7, or about 6 to about 7, or physiological pH, for example. Various buffers may be used to achieve the desired pH and maintain the pH during any incubation period. Illustrative buffers include, but are not limited to, borate, phosphate (e.g., phosphate buffered saline), carbonate, TRIS, barbital, PIPES, HEPES, MES, ACES, MOPS, and BICINE, for example.

The dilution medium may also comprise a lysing agent for lysing of cells. A lysing agent is a compound or mixture of compounds that disrupt the integrity of the membranes of cells thereby releasing intracellular contents of the cells. Examples of lysing agents include, but are not limited to, non-ionic detergents, anionic detergents, amphoteric detergents, low ionic strength aqueous solutions (hypotonic solutions), bacterial agents, aliphatic aldehydes, and antibodies that cause complement dependent lysis, for example. Various ancillary materials may be present in the dilution medium. All of the materials in the dilution medium are present in a concentration or amount sufficient to achieve the desired effect or function.

The amount of dilution medium combined with the blood sample is dependent on one or more of a number of factors such as, for example, the nature of the porous matrix, the nature of the blood sample, and the nature of the rare cells. In some examples in accordance with the principles described herein, the amount of dilution medium is about 5 mL to about 100 mL, or about 5 mL to about 80 mL, or about 5 mL to about 60 mL, or about 5 mL to about 50 mL, or about 5 mL to about 30 mL, or about 5 mL to about 20 mL, or about 5 mL to about 10 mL, or about 10 mL to about 100 mL, or about 10 mL to about 80 mL, or about 10 mL to about 60 mL, or about 10 mL to about 50 mL, or about 10 mL to about 30 mL, or about 10 mL to about 20 mL, or about 20 mL to about 100 mL, or about 20 mL to about 80 mL, or about 20 mL to about 60 mL, or about 20 mL to about 50 mL, or about 20 mL to about 30 mL, for example, based on 10 mL of the blood sample.

The porous matrix is a solid or semi-solid material and may be comprised of an organic or inorganic, water insoluble material. The porous matrix can have any of a number of shapes such as, for example, tubular (e.g., hollow fiber, spiral wound, and hollow fine fiber), track-etched, or planar or flat surface (e.g., strip, disk, film, membrane, and plate). The matrix may be fabricated from a wide variety of materials, which may be naturally occurring or synthetic, polymeric or non-polymeric, fibrous or non-fibrous. Examples, by way of illustration and not limitation, of such materials for fabricating a porous matrix include cellulose (including paper), nitrocellulose, cellulose acetate, polycarbonate, poly(vinyl chloride), polyacrylamide, polyacrylate, polyethylene, polypropylene, poly-(4-methylbutene), polystyrene, polymethacrylate, poly(ethylene terephthalate), nylon, and poly(vinyl butyrate), ceramic material, metallic material, for example, either used by themselves or in conjunction with one another and/or with other materials.

The size of the pores of the porous matrix is that which is sufficient to preferentially retain agglutinated rare cells while allowing the passage of other cells including non-rare cells through the pores in accordance with the principles described herein. The size of the pores of the porous matrix is dependent on the nature and size of the rare cells and the non-rare cells, the nature and size of the agglutinated rare cells, the pressure applied to the blood sample, for example. In some examples the average size of the pores of the porous matrix is about 1 µm to about 100 µm, or about 1 µm to about 75 µm, or about 1 µm to about 50 µm, or about 1 µm to about 20 µm, or about 1 µm to about 10 µm, or about 5 µm to about 100 µm, or about 5 µm to about 75 µm, or about 5 µm to about 50 µm, or about 5 µm to about 20 µm, or about 5 µm to about 10 µm, for example. The density of pores in the porous matrix is about 1% to about 80%, or about 10% to about 80%, or about 20% to about 80%, or about 50% to about 80%, or about 20% to about 70%, for example.

In some examples in accordance with the principles described herein, pressure is applied to the blood sample on the porous matrix to facilitate passage of non-rare cells through the membrane. The term "pressure" refers to pressure differences from normal atmospheric pressure and can be either positive pressure (increase in pressure relative to normal atmospheric pressure) or negative pressure (vacuum) (decrease in pressure relative to normal atmospheric pressure). The level of pressure applied is dependent on one or more of the nature and size of the non-rare cells, the nature and size of the agglutinated rare cells, the nature of the porous matrix, and the size of the pores of the porous matrix, for example. In some examples, the level of positive pressure applied is about 1 millibar to about 500 millibar, or about 1 millibar to about 400 millibar, or about 1 millibar to about 300 millibar, or about 1 millibar to about 200 millibar, or about 1 millibar to about 100 millibar, or about 1 millibar to about 50 millibar, or about 1 millibar to about 30 millibar, or about 1 millibar to about 25 millibar, or about 1 millibar to about 20 millibar, or about 1 millibar to about 15 millibar, or about 1 millibar to about 10 millibar, or about 5 millibar to about 30 millibar, or about 5 millibar to about 25 millibar, or about 5 millibar to about 20 millibar, or about 5 millibar to about 15 millibar, or about 5 millibar to about 10 millibar, for example. The level of negative pressure (vacuum) applied is the negative of the above ranges.

In some examples the pressure applied to the blood sample on the porous matrix is an oscillating pressure, which means that the pressure is applied intermittently at regular or irregular intervals, which may be, for example, about 1 second to about 600 seconds, or about 1 second to about 500 seconds, or about 1 second to about 250 seconds, or about 1 second to about 100 seconds, or about 1 second to about 50 seconds, or about 10 seconds to about 600 seconds, or about 10 seconds to about 500 seconds, or about 10 seconds to about 250 seconds, or about 10 seconds to about 100 seconds, or about 10 seconds to about 50 seconds, or about 100 seconds to about 600 seconds, or about 100 seconds to about 500 seconds, or about 100 seconds to about 250 seconds, for example. In this approach, pressure is oscillated at about 0 millibar to about 10 millibar, or about 1 millibar to about 10 millibar, or about 1 millibar to about 7.5 millibar, or about 1 millibar to about 5.0 millibar, or about 1 millibar to about 2.5 millibar, for example, during some or all of the application of pressure to the blood sample. Oscillating pressure is achieved using an on-off switch, for example, and may be conducted automatically or manually. High pressure drops are allowable depending on one or more of reservoir volume, sample volume and filtration rate.

Contact of the blood sample with the porous matrix is continued for a period of time sufficient to achieve an enrichment of the rare cells to non-rare cells on the porous matrix. The period of time is dependent on one or more of the nature and size of the non-rare cells, the nature and size of the agglutinated rare cells, the nature of the porous matrix, the size of the pores of the porous matrix, the level of pressure applied to the blood sample on the porous matrix, the volume to be filtered, the surface area of the filter, for example. In some examples, the period of contact is about 1 minute to about 1 hour, about 5 minutes to about 1 hour, or about 5 minutes to about 45 minutes, or about 5 minutes to about 30 minutes, or about 5 minutes to about 20 minutes, or about 5 minutes to about 10 minutes, or about 10 minutes to about 1 hour, or about 10 minutes to about 45 minutes, or about 10 minutes to about 30 minutes, or about 10 minutes to about 20 minutes, for example.

Any of a number of filtration techniques may be employed to carry out contact of the blood sample with a porous matrix. Such filtration techniques include, but are not limited to, microfiltration, ultrafiltration, or cross-flow filtration, for example. The porous matrix is generally part of a filtration module where the porous matrix is part of an assembly for convenient use during filtration.

Methods in accordance with the principles described herein achieve an increase in the ratio of rare cells to non-rare cells in a blood sample suspected of containing rare cells and non-rare cells of at least about 10 fold, or at least about 20 fold, or at least about 50 fold, or at least about 75 fold, or at least about 100 fold over the ratio of the rare cells to the non-rare cells in the original blood sample. In some examples, the increase of the ratio of rare cells to non-rare cells achieved in methods in accordance with the principles described herein is about 10 fold to about 200 fold, or about 10 fold to about 150 fold, or about 10 fold to about 100 fold, or about 25 fold to about 100 fold, or about 50 fold to about 100 fold, for example.

General Description of Assay Techniques for Cell Identification

Any suitable assay may be employed for determining the identity of a cell. The assays are conducted by combining the cells isolated by methods in accordance with the principles described herein with reagents for identifying the cells, which include an identification agent, that is, an agent that specifically recognizes or binds to an antigen associated with a cell. The nature of the reagents is dependent on the particular type of assay to be performed. In general, the assay is a method for the determination of the identity of a cell. The assay may be an immunoassay or a non-immunoassay. Various assay methods are discussed below by way of illustration and not limitation.

In many embodiments the reagents comprise, as an identification agent, at least one antibody specific for an antigen on the cell that is characteristic of the cell, that is, the antigen is known to be associated with the particular cell in question. This assay is generally referred to as an immunoassay as distinguished from assays that do not utilize an antibody, which are referred to as non-immunoassays. By the phrase "antibody for an antigen" is meant an antibody that binds specifically to the antigen and does not bind to any significant degree to other substances that would distort the analysis for the particular antigen.

Antibodies specific for an antigen for use in immunoassays to identify cells can be monoclonal or polyclonal. Such antibodies can be prepared by techniques that are well known in the art such as immunization of a host and collection of sera (polyclonal) or by preparing continuous hybrid cell lines and collecting the secreted protein (monoclonal) or by cloning and expressing nucleotide sequences or mutagenized versions thereof coding at least for the amino acid sequences required for specific binding of natural antibodies.

Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, and Fab', for example. In addition, aggregates, polymers, and conjugates of immunoglobulins or their fragments can be used where appropriate so long as binding affinity for a particular molecule is maintained.

Other reagents are included in the assay medium depending on the nature of the assay to be conducted. Such assays usually involve reactions between binding partners such as an antigen (protein) on a cell and a corresponding antibody or the binding between an antibody and a corresponding binding partner such as a second antibody that binds to the first antibody. The antibody and the antigen are members of a specific binding pair ("sbp member"), which is one of two different molecules, having an area on the surface or in a cavity, which specifically binds to and is thereby defined as complementary with a particular spatial and polar organization of the other molecule. The members of the specific binding pair will usually be members of an immunological pair such as antigen-antibody and hapten-antibody, although other specific binding pairs include, for example, biotin-avidin, hormones-hormone receptors, enzyme-substrate, nucleic acid duplexes, IgG-protein A, and polynucleotide pairs such as DNA-DNA, DNA-RNA.

As discussed above, specific binding involves the specific recognition of one of two different molecules for the other compared to substantially less recognition of other molecules. On the other hand, non-specific binding involves non-covalent binding between molecules that is relatively independent of specific surface structures. Non-specific binding may result from several factors including hydrophobic interactions between molecules. In many embodiments of assays, preferred binding partners are antibodies and the assays are referred to as immunoassays.

The immunoassays may involve labeled or non-labeled reagents. Immunoassays involving non-labeled reagents usually comprise the formation of relatively large complexes involving one or more antibodies. Such assays include, for example, immunoprecipitin and agglutination methods and corresponding light scattering techniques such as, e.g., nephelometry and turbidimetry, for the detection of antibody complexes. Labeled immunoassays include enzyme immunoassays, fluorescent-labeled immunoassays, fluorescence polarization immunoassays, radioimmunoassay, inhibition assay, induced luminescence, and fluorescent oxygen channeling assay, for example.

The assays can be performed either without separation (homogeneous) or with separation (heterogeneous) of any of the assay components or products. Homogeneous immunoassays include, but are not limited to, immunocytochemistry techniques, the direct fluorescent antibody test or the direct immunofluorescence test, homogeneous enzyme immunoassays including the EMIT® assay disclosed in U.S. Pat. No. 3,817,837; immunofluorescence methods such as those disclosed in U.S. Pat. No. 3,996,345; enzyme channeling immunoassays such as those disclosed in U.S. Pat. No. 4,233,402; and the fluorescence polarization immunoassay as disclosed, for example, in U.S. Pat. No. 5,354,693; for example.

Other enzyme immunoassays include the enzyme modulate mediated immunoassay; the substrate labeled fluorescence immunoassay; the combined enzyme donor immunoassays; homogeneous particle labeled immunoassays such as particle enhanced turbidimetric inhibition immunoassays and the particle enhanced turbidimetric immunoassay; for example. Other assays include the sol particle immunoassay; the disperse dye immunoassay; the metalloimmunoassay; the enzyme membrane immunoassays; luminoimmunoassays; acridinium ester label immunoassays using paramagnetic particles as a solid phase; for example. Other types of assays include immunosensor assays involving the monitoring of the changes in the optical, acoustic and electrical properties of an antibody-immobilized surface upon the binding of a hydrophobic drug. Such assays include, for example, optical immunosensor assays, acoustic immunosensor assays, semiconductor immunosensor assays, electrochemical transducer immunosensor assays, potentiometric immunosensor assays, amperometric electrode assays, and the like.

In many of the assays discussed herein for determination of a cell antigen, a label is employed; the label is usually part of a signal producing system ("sps"). The nature of the label is dependent on the particular assay format. A signal producing system usually includes one or more components, at least one component being a detectable label, which generates a detectable signal that relates to the amount of bound and/or unbound label, i.e. the amount of label bound or not bound to the analyte being detected or to an agent that reflects the amount of the analyte to be detected. The label is any molecule that produces or can be induced to produce a signal, and may be, for example, a fluorescer, a radiolabel, an enzyme, a chemiluminescer or a photosensitizer. Thus, the signal is detected and/or measured by detecting enzyme activity, luminescence, light absorbance or radioactivity, depending on the nature of the label.

Suitable labels include, by way of illustration and not limitation, dyes; fluorescers, such as fluorescein, isothiocyanate, rhodamine compounds, phycoerythrin, phycocyanin, allophycocyanin, o-phthaldehyde, and fluorescamine; enzymes such as alkaline phosphatase, glucose-6-phosphate dehydrogenase ("G6PDH"), β-galactosidase, and horseradish peroxidase; ribozyme; a substrate for a replicase such as QB replicase; promoters; complexes such as those prepared from CdSe and ZnS present in semiconductor nanocrystals known as Quantum dots; chemiluminescers such as isoluminol and acridinium esters, for example; sensitizers; coenzymes; enzyme substrates; radiolabels such as $^{125}I$, $^{131}I$, $^{14}C$, $^{3}H$, $^{57}Co$ and $^{75}Se$; particles such as latex particles, carbon particles, metal particles including magnetic particles, e.g., chromium dioxide ($CrO_2$) particles, and the like; metal sol; crystallite; liposomes; cells, etc., which may be further labeled with a dye, catalyst or other detectable group.

The label can directly produce a signal and, therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the signal producing system would then include all the components required to produce a measurable signal. Such other components may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in U.S. Pat. No. 5,185,243, columns 11-13, incorporated herein by reference.

The label or other sps members can be bound to a support or become bound to a molecule such as a cell that is disposed on a support. Cells may be bound to a solid support in any manner known in the art, provided only that the binding does not substantially interfere with the ability of an antigen on the cell to bind with an antibody. In some embodiments, the cells may be coated or covalently bound directly to the solid support Linking groups may also be used to covalently couple the solid support and the cells. Other methods of binding the cells are also possible. For instance, a solid support may have a coating of a binder for a small molecule such as, for example, avidin or an antibody, and a small molecule such as, e.g., biotin, hapten, etc., can be bound to the cells or vice versa. The binding of components to the surface of a support may be direct or indirect, covalent or non-covalent and can be accomplished by well-known techniques, commonly available in the literature.

The support may be comprised of an organic or inorganic, solid or fluid, water insoluble material, which may be transparent or partially transparent. The support can have any of a number of shapes, such as particle, including bead, film, membrane, tube, well, strip, rod, planar surfaces (such as, e.g., sheet, plate and slide), and fiber, for example. Depending on the type of assay, the support may or may not be suspendable in the medium in which it is employed. Examples of suspendable supports are polymeric materials such as latex; lipid bilayers or liposomes; oil droplets, and metallic supports such as, e.g., magnetic particles; for example. Other support compositions include polymers, such as nitrocellulose, cellulose acetate, poly(vinyl chloride), polyacrylamide, polyacrylate, polyethylene, polypropylene, poly(4-methylbutene), polystyrene, polymethacrylate, poly(ethylene terephthalate), nylon, and poly(vinyl butyrate), either used by themselves or in conjunction with other materials.

The label and/or other sps member may be bound to an sbp member or another molecule. For example, the label can be bound covalently to an sbp member such as, for example, an antibody, a receptor for an antibody, or a receptor that is capable of binding to a small molecule conjugated to an antibody. Bonding of the label to the sbp member may be accomplished by chemical reactions that result in replacing a hydrogen atom of the label with a bond to the sbp member or may include a linking group between the label and the sbp member. Other sps members may also be bound covalently to sbp members. For example, two sps members such as a fluorescer and quencher can each be bound to a different antibody that forms a specific complex with the analyte. Formation of the complex brings the fluorescer and quencher in close proximity, thus permitting the quencher to interact with the fluorescer to produce a signal.

The assays discussed above are normally carried out in an aqueous buffered medium at a moderate pH, generally that which provides optimum assay sensitivity. The pH for the assay medium will usually be in the range of about 4 to about 11, or in the range of about 5 to about 10, or in the range of about 6.5 to about 9.5. The pH will usually be a compromise between optimum binding of the binding members of any specific binding pairs, and the pH optimum for other reagents of the assay such as members of a signal producing system, for example. Various buffers may be used to achieve the desired pH and maintain the pH during the incubation period. Illustrative buffers include borate, phosphate, carbonate, TRIS, barbital, PIPES, HEPES, MES, ACES, MOPS, BICINE, and the like. Various ancillary materials may be employed in the assay methods. For example, in addition to buffers and preservatives, the medium may comprise stabilizers for the medium and for the reagents employed. In some embodiments, in addition to these additives, proteins may be included, such as albumins; quaternary ammonium salts; polyanions such as dextran sulfate; and binding enhancers, for example. All of the above materials are present in a concentration or amount sufficient to achieve the desired effect or function.

One or more incubation periods may be applied to the medium at one or more intervals including any intervals between additions of various reagents mentioned above. The medium is usually incubated at a temperature and for a time sufficient for binding of various components of the reagents to occur. Moderate temperatures are normally employed for carrying out the method and usually constant temperature, preferably, room temperature, during the period of the measurement. Incubation temperatures normally range from about 5° C. to about 99° C. or from about 15° C. to about 70° C., or about 20° C. to about 45° C., for example. The time period for the incubation is about 0.2 seconds to about 24 hours, or about 1 second to about 6 hours, or about 2 seconds to about 1 hour, or about 1 to about 15 minutes, for example. The time period depends on the temperature of the medium and the rate of binding of the various reagents. Temperatures during measurements will generally range from about 10° C. to about 50° C. or from about 15° C. to about 40° C.

The concentration of antigen that may be assayed generally varies from about $10^{-5}$ to about $10^{-17}$ M, or from about $10^{-6}$ to about $10^{-14}$ M. Considerations, such as whether the assay is qualitative, semi-quantitative or quantitative (relative to the amount of erythrocytophilic drug analyte present in the sample), the particular detection technique and the concentration of the analyte normally determine the concentrations of the various reagents.

The concentrations of the various reagents in the assay medium will generally be determined by the concentration range of interest of the antigen, the nature of the assay, the antibody affinity and avidity and antibody fragmentation, for example. However, the final concentration of each of the reagents is normally determined empirically to optimize the sensitivity of the assay over the range. Considerations such as the nature of a signal producing system and the nature of the analyte normally determine the concentrations of the various reagents.

While the order of addition may be varied widely, there will be certain preferences depending on the nature of the assay. The simplest order of addition is to add all the materials simultaneously and determine the effect that the assay medium has on the signal as in a homogeneous assay. Alternatively, the reagents can be combined sequentially. Optionally, an incubation step may be involved subsequent to each addition as discussed above. The length of the incubation period is that which is sufficient to accomplish the desired function.

Specific Embodiments of Assays for Cell Identification

Specific embodiments of assays that may be employed to identify cells in an enriched cell preparation in accordance with the principles described herein are discussed below by way of illustration and not limitation.

In one example, an immunocytochemistry technique is employed to determine whether or not one or more antigens specific for respective rare cells of interest is present on the rare cells prepared in accordance with the principles described herein. The rare cell preparation is placed on a solid support, which may be, for example, a microscope slide. The rare cell preparation may be removed from a filter membrane, for example, and placed on a solid support for examination or the filter membrane itself may be placed on the solid support. The rare cell preparation may be treated to fix the cells and/or to permeabilize the cells, if desired.

Fixation of the rare cells immobilizes the cells and preserves cell structure and maintains the cells in a condition that closely resembles the cells in an in vivo-like condition and one in which the antigens of interest are able to be recognized by a specific antibody. The amount of fixative employed is that which preserves the cells but does not lead to erroneous results in a subsequent assay. The amount of fixative depends on one or more of the nature of the fixative and the nature of the rare cells, for example. In some examples, the amount of fixative is about 0.05% to about 0.15%, or about 0.05% to about 0.10%, or about 0.10% to about 0.15%, for example, by volume of the blood sample. Agents for carrying out fixation of the rare cells include, but are not limited to, cross-linking agents such as, for example, an aldehyde reagent (such as, e.g., formaldehyde, glutaraldehyde, and paraformaldehyde); an alcohol (such as, e.g., C1-C5 alcohols such as methanol, ethanol and isopropanol); a ketone (such as a C3-C5 ketone such as acetone); for example. The designations C1-C5 or C3-C5 refer to the number of carbon atoms in the alcohol or ketone. One or more washing steps may be carried out on the fixed cells using a buffered aqueous medium.

If necessary after fixation, the rare cell preparation is also subjected to permeabilization. In some instances, a fixation agent such as, for example, an alcohol (e.g., methanol or ethanol) or a ketone (e.g., acetone) also results in permeabilization and no additional permeabilization step is necessary. Permeabilization provides access through the cell membrane to antigens of interest. The amount of permeabilization agent employed is that which disrupts the cell membrane and permits access to the antigens. The amount of permeabilization agent depends on one or more of the nature of the permeabilization agent and the nature and amount of the rare cells, for example. In some examples, the amount of permeabilization agent is about 0.1% to about 0.5%, or about 0.1% to about 0.4%, or about 0.1% to about 0.3%, or about 0.1% to about 0.2%, or about 0.2% to about 0.5%, or about 0.2% to about 0.4%, or about 0.2% to about 0.3%, for example. Agents for carrying out permeabilization of the rare cells include, but are not limited to, an alcohol (such as, e.g., C1-C5 alcohols such as methanol and ethanol); a ketone (such as a C3-C5 ketone such as acetone); a detergent (such as, e.g., saponin, TRITON® X-100, and TWEEN®-20); for example. One or more washing steps may be carried out on the permeabilized cells using a buffered aqueous medium.

In the immunocytochemistry technique, a labeled antibody specific for an antigen on a rare cell is employed for each suspected different rare cell in the rare cell preparation obtained in accordance with the principles described herein. The labels are fluorescent labels and a different fluorescent label is employed for each different rare cell such that multiple fluorescent-labeled antibodies may be employed in any one assay conducted on an isolated rare cell preparation obtained in accordance with the principles described herein.

Following fixation and permeabilized, the rare cell preparation is contacted with an aqueous medium containing one or more labeled antibodies as described above. The aqueous medium may be an assay medium as described above and the amount of each labeled antibody is that which is sufficient to identify each of the rare cells in the rare cell preparation. In some examples, the amount of each labeled antibody is in excess of the suspected amount of the rare cells in the rare cell preparation. The rare cells are incubated with the labeled antibodies under conditions that permit binding of the labeled antibodies to their respective antigens. Such conditions are discussed above regarding assays in general. After incubation, the rare cell preparation is subjected to one or more washing steps using an aqueous buffered medium to remove unbound labeled antibodies.

A fluorescent DNA stain such as, for example, 4',6-diamidino-2-phenylindole, propidium iodide, ethidium bromide, SYBR® Green I, VISTRA™ GREEN, SYTO® GREEN, SYBR® Gold, YO-PRO-1™, TOTO-3™, TO-PRO-3™, NUCLEAR-ID™ Red, or Hoechst dye, is employed to enhance contrast in rare cell preparation image during microscopic examination. After staining, one or more washing steps may be carried out on the cells using a buffered aqueous medium. The cells are then examined using a fluorescent microscope and each of the different fluorescent labels is used in the direct detection of a respective rare cell in the rare cell preparation.

Alternatively, in the above procedure unlabeled antibodies may be employed and the respective antibodies are detected indirectly employing a specific binding member for each of the respective antibodies where the different specific binding members are labeled with a respective fluorescent label or a respective enzyme label (such as, e.g., thiol-specific antioxidant (TSA enzyme)), for example. The respective labels of the specific binding members are detected by appropriate means. The specific binding members may be, for example, an antibody specific for each of the respective unlabeled antibodies used for binding to a respective antigen of a rare cell.

Kits for Conducting Assays on Rare Cell Preparations

The reagents for conducting a particular assay may be present in a kit useful for conveniently performing an assay for the determination of one or more rare cell types. In one embodiment a kit comprises in packaged combination a fibrin-formation-arresting agent for arresting fibrin formation in accordance with the principles described herein. The kit may also comprise one or more labeled or unlabeled antibodies specific for an antigen that is characteristic of a particular rare cell that may be present in a sample to be tested. Where unlabeled antibodies are employed, the kit may also contain one or more labeled specific binding pair members for each of the respective unlabeled antibodies. Other reagents for performing an assay may also be included in the kit, the nature of such reagents depending upon the particular assay format to be employed. The reagents may each be in separate containers or various reagents can be combined in one or more containers depending on the cross-reactivity and stability of the reagents. The kit can further include other separately packaged reagents for conducting an assay such as additional specific binding pair members, ancillary reagents such as an ancillary enzyme substrate, binders, containers for collection of samples, and supports for cells such as, for example, microscope slides, for conducting an analysis, for example.

The relative amounts of the various reagents in the kits can be varied widely to provide for concentrations of the reagents that substantially optimize the reactions that need to occur during the present methods and further to optimize substantially the sensitivity of an assay. Under appropriate circumstances one or more of the reagents in the kit can be provided as a dry powder, usually lyophilized, including excipients, which on dissolution will provide for a reagent solution having the appropriate concentrations for performing a method or assay. The kit can further include a written description of a method utilizing reagents in accordance with the principles described herein.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The following examples further describe the specific embodiments of the invention by way of illustration and not limitation and are intended to describe and not to limit the scope of the invention. Parts and percentages disclosed herein are by volume unless otherwise indicated.

EXAMPLES

All chemicals may be purchased from the Sigma-Aldrich Company (St. Louis Mo.) unless otherwise noted.

Abbreviations $K_3$EDTA=potassium salt of ethylenediaminetetraacetate
WBC=white blood cells
RBC=red blood cells
FITC=fluorescein isothiocyanate
DAPI=4',6-diamidino-2-phenylindole
DABCO=1,4-diazabicyclo[2.2.2]octane
min=minute(s)
μm=micron(s)
mL=milliliter(s)
mg=milligrams(s)
μg=microgram(s)
PBS=phosphate buffered saline (3.2 mM $Na_2HPO_4$, 0.5 mM $KH_2PO_4$, 1.3 mM KCl, 135 mM NaCl, pH 7.4)
mBar=millibar
RT=room temperature Whole blood specimens for testing were prepared by collection of blood from normal subjects lacking any rare cells due to disease. The blood samples (7-10 mL) were collected into VACUTAINER® tubes (Becton, Dickinson and Company, Franklin Lakes N.J.) containing $K_3$EDTA. WBC were about $10^7$ per 10 mL blood and RBC were about $5 \times 10^{10}$ per 10 mL of blood. Cultured rare cells, which were either cultured cancer cells, endothelial cells or epithelial cells (ATCC Manassas, Va.), were added to the blood samples at a level of 10 cells per 10 mL of blood sample. Therefore, before filtration, the rare cell to all normal cell ratio was 0.00000002% and the rare cell to WBC ratio was 0.00001%. Fibrin at 0.2 to 10 mg/L was added to some samples in accordance with the principles described herein. In some samples additional paraformaldye at 0.05% by volume of the blood sample was added.

Within one day after storage at 25° C., the blood samples were filtered through a membrane having an average pore size of 8 μm according to a method disclosed in U.S. Patent Application Publication No. 2012/0315664, the relevant portions of which are incorporated herein by reference. During filtration, the sample on the membrane was subjected to a negative mBar, that is, a decrease greater than about −30 mBar from atmospheric pressure. The vacuum applied varies from 1 to −30 mBar as the volume of the sample reduces from during filtration. High pressure drops are allowable dependent on reservoir and sample volume and filtration rate. Just prior to filtration, a sample (7-10 mL) was transferred to a 50 mL Falcon tube, which was filled to 20 mL with cold PBS. The Falcon tubes were manually overturned twice and subjected to centrifugation for 10 min., at 400×g at 20° C. The diluted sample was placed into the filtration station without mixing and the diluted sample was filtered through the membrane. Following the filtration, the membrane was washed with PBS, and the sample was fixed with formaldehyde, washed with PBS, subjected to permeabilization using of 0.2% TRITON® X100 in PBS and washed again with PBS.

Cells captured on the membrane were detected with an immunocytochemistry (ICC) procedure based on the binding of specific antibodies to specific proteins or antigens in cells. A blocking buffer of 10% casein in PBS was dispensed on the membrane. After an incubation period of 5 min, the membrane was washed with PBS to block non-specific binding to the membrane. Next, an antibody-conjugate mix was dispensed to the membrane followed by an incubation period of 20 min at RT. The mixture of antibody conjugates (in 10% casein in PBS) included anti-fibrin antibody (reactive to D-Dimer) conjugated to FITC at 10 μg/mL, anti-cancer cell antibody (reactive to CK8/18) conjugated to Dy550 at 15 μg/mL, and anti-CD45 antibody (used for WBC) conjugated to Dy650 at 20 μg/mL. The mixture of antibody conjugates can include anti-endothelial cell antibody (reactive to CT105) conjugated to Dy550, or anti-epithelial cell antibody (reactive to EPCAM) conjugated to Dy550 at 15 μg/mL, in place of the anti-cancer cell antibody (reactive to CK8/18) conjugated to Dy550. Unbound antibody was washed away (PBS+0.05% TWEEN® 20) and DAPI (0.8 μg/mL in PBS), a fluorescent DNA stain was added to stain the nuclei of the cells. A last wash step with PBS was performed, followed by cover media to help preserve the fluorescent intensity of the probes. Slides were made with DABCO as a cover slip medium (0.25 g DABCO to 9 mL glycerol and 1 ml 10×PBS).

Slides were then placed on a slide holder of a fluorescent microscope (Leica DM5000 (Leica Microsystems GmbH, Wetzlar, Germany)) where images were captured during the automated scanning of the membrane for each of the fluorescent probes used for detection of targeted cells. Antibody-conjugates became bound to the protein or antigen of a cell, and the fluorescent labels were detected by using a fluorescent microscope with excitation, emission, and cut-off filters specific for each label. Multiple fluorescent labels, each with a different specific antibody, are used to detect multiple antigens or proteins in the isolated cells.

Cells were then characterized by scanning the membrane by fluorescence microscopics conducted with a Leica DM5000 using the filter sets for respective fluorophore labels used in the antibody-conjugates above, namely, FITC, DyLight 550 (ThermoFisher Scientific, Inc., Waltham Mass.), DyLight 650 (ThermoFisher Scientific, Inc.) or DAPI. Enrichment of rare cells achieved was measured by counting the rare cells (either CK or CD105 or EpCAM positive) and comparing to the count of the normal cells remaining on the membrane. RBC were either lysed or passed through the membrane; all normal cells were WBC (CD45 positive).

The results for six sample types are summarized below in Table 1. The results are categorized as whole blood with and without chemical paraformaldehyde as a fibrin-formation-arresting agent and whole blood without added fibrin (not in accordance with the principles described herein) and with additional fibrin (in accordance with the principles described herein) to arrive at an amount between 0.2 mg/L to about 10 mg/L The enrichment ratio, the percentage of cells with large fibrin aggregates on their surface and the percentage of cells agglutinated to other cells were measured.

TABLE 1

| Sample Type | Fibrin Added | Paraformaldehyde (%) | % cells with fibrin on surface | Enrichment ratio Rare/Normal |
|---|---|---|---|---|
| 1 | 0 | 0.05 | 0.3 | 0.0020 |
| 2 | 0 | 0.05 | 1.4 | 0.0050 |
| 3 | 0.2 | 0.05 | 2.5 | 0.0140 |
| 4 | 0.2 | 0 | 5.3 | 0.1001 |
| 5 | 2.0 | 0.05 | 8.2 | 0.1818 |
| 6 | 10 | 0.05 | 32.4 | 0.0769 |

Figure 2:
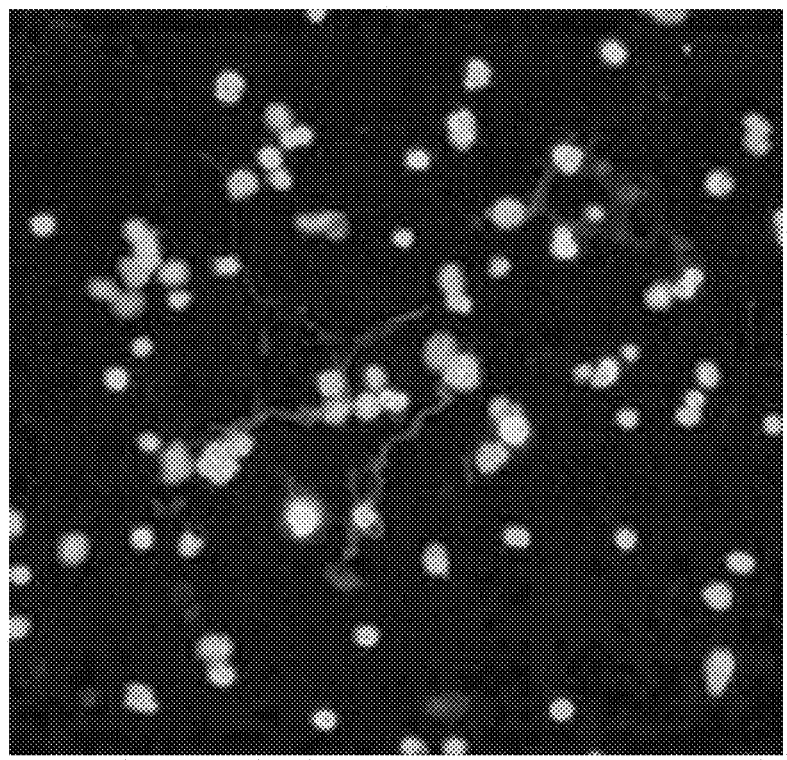
FIG. 2 represents a visualization of cells and fibrin using direct immunofluorescence based on experiments described in the Examples section below. The visualization corresponds to the results summarized in Table 1 for Sample Type 2, which is not in accordance with the principles described herein but is provided for purposes of comparison.

Referring to FIG. 1, for Sample Type 3, large fibrin aggregates and small fibrin spindles were observed on the membrane after filtration of whole blood with cultured cancer cells. The results show increased fibrin coverage of cells and show cancer cells (arrow) that are trapped in the fibrin in accordance with the principles described herein. FIG. 2 represents results that are not in accordance with the principles described herein but are presented for purposes of comparison; in this example, no fibrin was added.

The above results demonstrate that the separation efficiency depended on the amount of fibrin added. For Sample Types 1 and 2, the enrichment ratio showed an increase from 0.0020% to 0.0050% with a change in the percentage of cells with fibrin on the cell surface from 0.3% to 1.4%. Sample Types 1 and 2 had less than 1.4% fibrin detected on the cells and the lowest rare cell/WBC enrichment of <=0.005. While improved over 0.000009% ratio of rare cell/WBC before any separation, this ratio was below the desired >=0.01% enrichment ratio found when fibrin was added in accordance with the principles described herein. Sample types 1 and 2 represent collections from different patients, who have variances in fibrin. Sample type 1 represents a typical patient (80% of patients). Sample type 2 is from a patient with on-going fibrin formation prior to blood draw. The differences in fibrin formation for these two patient types demonstrates the problem that arises if endogenous fibrin (that is, fibrin that forms from endogenous components of the blood coagulation cascade) is not arrested and fibrin is not added. Sample types 1 and 2 also show that typical endogenous fibrin level is below 0.2 mg/L.

The addition of 0.2 mg/L of fibrin to Sample Type 3 allowed 2.5% of cells with fibrin and a significantly improved enrichment ratio of 0.0140%. The enrichment ratio further increased to 0.1818% with the addition of 2 mg/L of fibrin in Sample Type 5. The enrichment ratio decreased to 0.0769% with addition of 10 mg/L fibrin to the blood sample as shown in Sample Type 6, which exhibited some cell-cell agglutination. Sample Types 3-5 exhibited less cell-cell agglutination. Thus, within the range of added fibrin of 0.2 mg/L to 10 mg/L, enrichment ratio is significantly enhanced while cell-cell agglutination is minimized.

For Sample Types 3-5 where the added fibrin content is 0.2 mg/L to 2.0 mg/L and >2.5% of cells were covered with large fibrin, aggregates of cells with fibrin are too large (>50 μm) to pass through micron size pores. As depicted in FIG. 1, small fibrin spinals (1-10 μm) were observed at higher magnification on most rare cells. Therefore, the filtration of cells with fibrin >2.0 mg/L was independent of pore size and cell deformation. The pores of a membrane can be larger than the average diameter of a cancer cell and cells with large fibrin on the surface at levels in accordance with the principles described herein will not pass through the membrane and are retained on its surface while other cells pass through thereby resulting in enrichment of the ratio of rare cells to non-rare cells.

The above experiments demonstrate that filtration methods of rare cells in whole blood prepared in accordance with the principles described herein are not isolating individual rare cells but aggregates of rare cells and fibrin and that the fibrin content is an important factor to achieve desired enrichments. As clotting is a natural process, some degree of fibrin formation occurs in all filtration methods, but not to a level to achieve desired enrichments nor in a controlled amount to achieve a consistent separation. An amount of added fibrin above 0.2 mg/L and 2.5% or more of rare cells forming fibrin aggregates results in separation of rare cells from non-rare cells. Fibrin causes rare cells to behave as rare cells with fibrin on their surface rather than as individual cells as is the case with non-rare cells, which do not appear to be as sensitive to fibrin aggregation as rare cells. Thus, fibrin coverage (level of fibrin formation) on the surface of rare cells is an important factor in realizing enrichment by filtration.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. A method of increasing a ratio of rare cells to non-rare cells in a blood sample suspected of containing rare cells and non-rare cells, the method comprising:
   (a) adding in combination to the blood sample:
      (i) a platelet deactivation agent,
      (ii) a fibrin-formation-arresting agent, and
      (iii) exogenous fibrin in an amount ranging from about 0.2 mg/L to about 10 mg/L to thereby yield a level of agglutination of the rare cells, the level of agglutination of the rare cells ranging from about 2.5% to about 100% based on an amount of surface area of the rare cells covered with large fibrin thereby preparing a treated blood sample comprising agglutinated rare cells; and
   (b) contacting the treated blood sample with a porous matrix such that the agglutinated rare cells are preferentially retained on the porous matrix.

2. The method according to claim 1 wherein contacting the treated blood sample with a porous matrix comprises disposing the treated blood sample on a side of the porous matrix and applying pressure to the disposed treated blood sample.

3. The method according to claim 2 wherein the pressure applied is about 1 millibar to about 30 millibar.

4. The method according to claim 2 wherein the pore size of the porous matrix is about 1 μm to about 100 μM.

5. The method according to claim 1 wherein the rare cells are cancer cells.

6. The method according to claim 1 wherein prior to contacting the treated blood sample with the porous matrix the treated blood sample is diluted with a dilution medium.

7. The method according to claim 6 wherein the dilution medium is an aqueous buffered medium.

8. The method according to claim 1 wherein the agglutinated rare cells are subjected to an identification method.

9. The method according to claim 1 wherein steps (a) and (b) are performed simultaneously.

10. A method of increasing a ratio of cancer cells to non-cancer cells in a blood sample suspected of containing cancer cells and non-cancer cells, the method comprising:
    (a) preparing a treated blood sample comprising agglutinated cancer cells by combining the blood sample with a combination comprising:
        (i) a platelet deactivation agent,
        (ii) a fibrin-formation-arresting agent, and
        (iii) exogenously-added fibrin in an amount ranging from about 0.2 mg/L to about 10 mg/L to cause agglutination of the rare cells, the agglutination of the rare cells being in an amount of about 2.5% to about 100% based on an amount of surface area of the rare cells covered with large fibrin,
    (b) diluting the treated blood sample with a dilution medium; and
    (c) disposing the diluted treated blood sample on a side of a porous matrix and applying pressure to the disposed treated blood sample wherein the agglutinated cancer cells are preferentially retained on the porous matrix.

11. The method according to claim 10 wherein the pressure applied is about 1 millibar to about 30 millibar.

12. The method according to claim 10 wherein the pore size of the porous matrix is about 1 μm to about 100 μm.

13. The method according to claim 10 wherein the agglutinated cancer cells are subjected to an identification method.

14. A method of identifying at least one rare cell type in a blood sample suspected of containing the rare cell type, the method comprising:
    (a) adding in combination to the blood sample;
        a platelet deactivation agent,
        a fibrin-formation-arresting agent, and
        exogenous fibrin in an amount of about 0.2 mg/L to about 7.5 mg/L to cause agglutination of the rare cells, the agglutination of the rare cells ranging from about 2.5% to about 100% based on an area of an outer surface of the rare cells and to prepare a treated blood sample comprising agglutinated rare cells;
    (c) diluting the treated blood sample with a dilution medium,
    (d) contacting the diluted treated blood sample with a porous matrix such that the agglutinated rare cells are preferentially retained on the porous matrix; and
    (e) contacting the agglutinated rare cells with an identification agent.

15. The method according to claim 14 wherein contacting the diluted treated blood sample with a porous matrix comprises disposing the treated blood sample on a side of the porous matrix having a pore size of about 1 μm to about 100 μm, and applying pressure to the disposed blood sample wherein the pressure applied is about 1 millibar to about 30 millibar.

16. The method according to claim 14 wherein the identification agent is a labeled specific binding member for the rare cells.

17. The method according to claim 14 wherein the rare cells are cancer cells.

* * * * *